(12) United States Patent
Shen et al.

(10) Patent No.: US 9,084,822 B2
(45) Date of Patent: Jul. 21, 2015

(54) SOLID FORM AND METHOD FOR PREPARING THE SAME

(71) Applicant: Industrial Technology Research Institute, Chutung, Hsinchu (TW)

(72) Inventors: Hsin-Hsin Shen, Zhudong Township, Hsinchu County (TW); Yu-Bing Liou, Hsinchu (TW); Chin-Fu Chen, New Taipei (TW); Li-Hsin Lin, Hsinchu (TW); Hsiu-Hua Huang, New Taipei (TW); Ying-Hsueh Chao, Tainan (TW); Meng-Yow Hsieh, Taipei (TW); Miao-Tzu Chen, Zhudong Township, Hsinchu County (TW); Chih-Bing Hung, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 21 days.

(21) Appl. No.: 13/871,491

(22) Filed: Apr. 26, 2013

(65) Prior Publication Data
US 2014/0187591 A1   Jul. 3, 2014

(30) Foreign Application Priority Data

Dec. 28, 2012   (TW) .............................. 101150896 A (51) Int. Cl.
| A61L 27/54 | (2006.01) |
| A61K 47/34 | (2006.01) |
| A61K 9/00  | (2006.01) |

(52) U.S. Cl.
CPC .............. *A61K 47/34* (2013.01); *A61K 9/0024* (2013.01)

(58) Field of Classification Search
CPC ... A61K 47/18; A61K 47/34; C08G 2210/00; C08G 2250/00
See application file for complete search history.

(56) References Cited

U.S. PATENT DOCUMENTS

| 211,959 | A | 2/1879 | Blood |
| 5,529,987 | A | 6/1996 | Gallina |
| 5,643,591 | A | 7/1997 | Mehra et al. |
| 8,133,513 | B2 | 3/2012 | Hayashi et al. |
| 8,211,959 | B2 | 7/2012 | Shen et al. |
| 2004/0147466 | A1 | 7/2004 | Barman et al. |
| 2008/0200948 | A1 | 8/2008 | Utecht et al. |
| 2010/0166863 | A1* | 7/2010 | Shen et al. ..................... 424/484 |
| 2011/0008442 | A1 | 1/2011 | Zawko et al. |

FOREIGN PATENT DOCUMENTS

TW    201024338 A1   7/2010

OTHER PUBLICATIONS

Huettenrauch, R., and S. Fricke. "On the Significance of the Degree of Order of the Liquid-Phase for the Release of Active Agents from Ointments." Pharmazie 37.9 (1982): 671-672; STN AN=1983:22181 CAPLUS (accessed Sep. 20, 2014).*
Huettenrauch, R., S. Fricke, and P. Zielke. "The effect of water structure on the hydrogelling of polymethylmethacrylates. The ice theory of hydrogels." Die Pharmazie 40.6 (1985): 427-427; STN AN=1985:583481 CAPLUS (accessed Sep. 20, 2014).*
Sanabria-DeLong, Naomi, et al. "Controlling hydrogel properties by crystallization of hydrophobic domains." Macromolecules 39.4 (2006): 1308-1310.*
Steed, Jonathan W. "Anion-tuned supramolecular gels: a natural evolution from urea supramolecular chemistry." Chemical Society Reviews 39.10 (2010): 3686-3699.*
H. Seager, "Drug-Delivery Products and the Zydis Fast-Dissolving Dosage Form," J. Pham. Pharmacol., vol. 50, pp. 375-382 (1998).
Zhou et al., "Solubility of Cellulose in NaOH/Urea Aqueous Solution," Polymer Journal, vol. 32, No. 10, pp. 866-870 (2000).
Yabuuchi et al., "A New Urea Gelator: Incorporation of Intra- and Intermolecular Hydrogen Bonding for Stable 1D Self-Assembly," Org. Biomol. Chem., vol. 1, pp. 3464-3469 (2003).
Zhou et al., "Hydrogels Prepared from Unsubstituted Cellulose in NaOH/Urea Aqueous Solution," Macromol. Biosci., vol. 7, pp. 804-809 (2007).
Suzuki et al., "Supramolecular Organogel Fomation Triggered by Acid-Base Interaction in Two-Component System Consisting of L-lysine Derivative and Aliphatic Acids," New J. Chem., vol. 31, pp. 1654-1660 (2007).
Radu Custelcean, "Crystal Engineering with Urea and Thiourea Hydrogen-Bonding Groups," Chem. Commun., pp. 295-307 (2008).
Tiwari et al., "Solid Dispersions: An Overview to Modify Bioavailability of Poorly Water Soluble Drugs," Intl. J. of Pharm Tech Res., vol. 1, No. 4, pp. 1338-1349 (10-12/2009).
Duan et al., "Isomeric Effect in the Self-Assembly of Pyridine-Containing L-glutamic Lipid: Substituent Position Controlled Morphology and Supramolecular Chirality," Chem. Commun., vol. 47, pp. 5569-5571 (2011).

(Continued)

*Primary Examiner* — Bethany Barham
*Assistant Examiner* — Peter Anthopolos
(74) *Attorney, Agent, or Firm* — Muncy, Geissler, Olds & Lowe, P.C.

(57) ABSTRACT

The disclosure provides a solid form and a method for preparing the same. The solid form consists essentially of a biodegradable copolymer and an amide-containing compound. The biodegradable copolymer is semi-crystalline due to the dipole-dipole interaction between the biodegradable copolymer and the urea. The method for preparing the above solid form includes: dissolving a biodegradable copolymer and an amide-containing compound in water at a first temperature, obtaining a solution; cooling the solution at a second temperature to form a solid mixture; and the solid mixture is subjected to a freeze-drying process at a third temperature.

6 Claims, 6 Drawing Sheets

(56) References Cited

OTHER PUBLICATIONS

Buerkle et al., "Supramolecular Gels Formed from Multi-Component Low Molecular Weight Species," Chem. Soc. Rev., vol. 41, pp. 6089-6102 (2012).

Heller et al, "Theory and Practice of Controlled Drug Delivery From Bioerodible Polymers," Controlled Release of Bioactive Materials, 1980, p. 1-17.

Office Action issued on Nov. 11, 2014 by the Taiwanese Patent Office in corresponding TW Patent Application No. 101150896.

* cited by examiner

SOLID FORM AND METHOD FOR PREPARING THE SAME

CROSS REFERENCE TO RELATED APPLICATIONS

This application is based upon and claims the benefit of priority from the prior Taiwan Patent Application No. 101150896, filed on Dec. 28, 2012, the entire contents of which are incorporated herein by reference.

BACKGROUND

1. Technical Field

The technical field relates to a solid form, and in particular, relates to a solid form with a rapid dissolution rate 2. Related Art In most instances, a substitutive tissue must be used to recover the functionality of body tissue damaged by disease, unless the original tissues have a high inherent regeneration capacity. The unavailability of acceptable human donor organs, and the low rate of long term success due to host versus graft rejections, are the main challenges now facing the field of tissue and organ transplantation.

In recent years, biodegradable hydrogel have been applied in medical treatments, serving as a bone bonding reconstruction, implantable drug release carrier, or drug delivery. However, in clinical applications and commercialization, due to the short shelf life and low stability of the hydrogel, the applications of hydrogel are greatly limited.

Although the hydrogel can be stored in the form of a hydrogel precursor, it takes a long period of time (such as hours or days) until a hydrogel precursor is dissolved completely in water to form hydrogen, resulting in inconvenience to users.

There is, therefore, still a need for a novel method for storing a hydrogel in order to solve the above problems.

SUMMARY

An exemplary embodiment of the disclosure provides a solid form, consisting essentially of a biodegradable copolymer and an amide-containing compound, wherein the biodegradable copolymer is in a semi-crystalline state due to the dipole-dipole interaction between the biodegradable copolymer and the amide-containing compound Another exemplary embodiment of the disclosure provides a method for preparing the aforementioned solid form, including: dissolving a biodegradable copolymer and an amide-containing compound in water at a first temperature, obtaining a solution; cooling the solution at a second temperature to form a solid mixture; and the solid mixture is subjected to a freeze-drying process at a third temperature.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
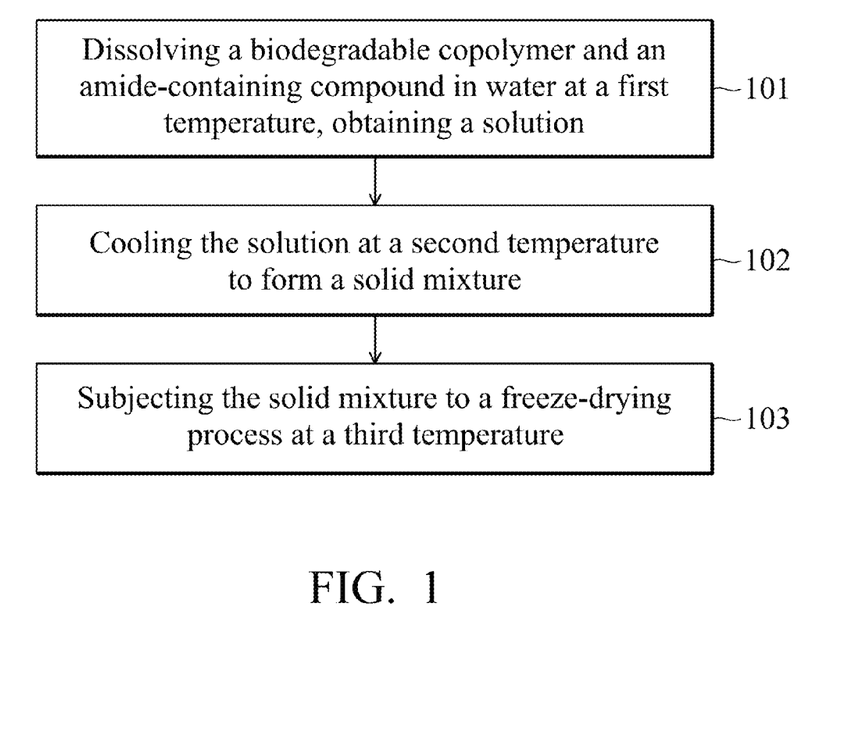
FIG. 1 shows a flow chart illustrating process steps according to a method for preparing a solid form according to an embodiment of the disclosure.

The disclosure provides a method for preparing a solid form. FIG. 1 shows a flow chart illustrating process steps according to a method for preparing a solid form according to an embodiment of the disclosure. First, a biodegradable copolymer and an amide-containing compound are dissolved in water at a first temperature, obtaining a solution (step 101), wherein the weight ratio of the biodegradable copolymer is 52-83 wt %, and the weight ratio of the amide-containing compound is 17-48 wt %, based on the weight of the biodegradable copolymer and the amide-containing compound. The first temperature is from 1 to 10° C. Particularly, the amide-containing compound can be a urea niacinamide or combinations thereof. Next, the solution is cooled to a second temperature to form a solid mixture (step 102), wherein the second temperature is from −15 to −60° C. Finally, the solid mixture is subjected to a freeze-drying process at a third temperature (step 103) in order to remove water, wherein the third temperature is from −15 to −40° C.

The aforementioned biodegradable copolymer can be a di-block or tri-block copolymer prepared from a hydrophobic polymer and a hydrophobic polymer via a copolymerization process, wherein the hydrophilic polymer comprises polyethylene glycol (PEG), or methoxy-poly(ethylene glycol) (mPEG). The hydrophobic polymer can be poly(lactide-co-glycolide) (PLGA), poly(propionic-co-lactic (PPLA), poly (valeric-co-lactic) (PVLA), or poly(caproic-co-lactic (PCLA). According to some embodiments of the disclosure, the biodegradable copolymer can be PEG-PLGA, PEG-PLGA-PEG, PLGA-PEG-PLGA, or combinations thereof. The term PEG means a hydrophilic polyethylene glycol (PEG) polymer, such as polyethylene glycol (PEG), or methoxy-poly(ethylene glycol) (mPEG)(methoxy-poly(ethylene glycol), mPEG). The hydrophilic polyethylene glycol (PEG) polymer can have a molecular weight of between 350-2000 g/mole. The term PLGA means hydrophobic poly(lactic-co-glycolic acid), and can be derived from D,L-Lactide, D-Lactide, L-Lactide, D,L-Lactic D-Lactic acid, L-Lactic acid, glycolide, β-propiolactone, δ-valerolactone, or ε-caprolactone, such as poly(lactide-co-glycolide) (PLGA), poly(propionic-co-lactic (PPLA), poly(valeric-co-lactic) (PVLA), or poly(caproic-co-lactic) (PCLA). The hydrophobic poly(lactic-co-glycolic acid) can have a molecular weight of between 1000-3500 g/mole. According to another embodiment of the disclosure, the biodegradable copolymer includes a copolymer represented by Formula (I) or Formula (II) as follows:

A-B-BOX-B-A   Formula (I); and

B-A-B-(BOX-B-A-B)$_n$-BOX-B-A-B   Formula (II)

wherein A comprises a hydrophilic polyethylene glycol polymer, B comprises a hydrophobic polyester polymer, BOX is a bifunctional group monomer of 2,2'-Bis(2-oxazoline) and used for coupling the blocks A-B or B-A-B, and n is an integer and the same or more than 0. The hydrophilic polyethylene glycol polymer (A) can be polyethylene glycol polymer or methoxy-poly(ethylene glycol). The hydrophilic polyethylene glycol polymer (A) can have a molecular weight of 300-5000. Further, the hydrophobic polyester polymer (B) can be polymers or copolymers derived from D,L-Lactide, D-Lactide, L-Lactide, D,L-Lactic acid, D-Lactic acid, L-Lactic acid, glycolide, β-propiolactone, δ-valerolactone, or ε-caprolactone, such as poly(lactide-co-glycolide) (PLGA), poly(propionic-co-lactic (PPLA), poly(valeric-co-lactic) (PVLA), or poly(caproic-co-lactic) (PCLA). The hydrophobic polyester polymer (B) can have a molecular weight of 500-5000. For example, the hydrophobic polyester polymer (B) can be poly(lactide-co-glycolide) which is a copolymer by polymizing the poly(lactic acid) and poly(glycolide acid), wherein the poly(lactic acid) has a mole percent of 50-90 mol % and the poly(glycolide acid) a mole percent of 10-50 mol %, based on the total mole percent of poly(lactic acid) and poly(glycolide acid).

In an embodiment of the disclosure, one end of the hydrophobic polyester polymer (B) which is not bonded with the hydrophilic polyethylene glycol polymer (A) can have an end capping/coupling functional group, wherein the hydrophobic polyester polymer (B) is bonded with the BOX via the end capping/coupling functional group. The end capping/coupling functional group can be derived from an end capping/coupling agent, wherein the end capping/coupling agent comprises an anhydride such as succinic anhydride, maleic anhydride, phthalic anhydride, or sebacic anhydride.

The solid form of the disclosure prepared from the aforementioned steps 101 to 103 consists essentially of the molecular-level biodegradable copolymer; and the molecular-level amide-containing compound. The weight ratio of the biodegradable copolymer is 52-83 wt %, the weight ratio of the amide-containing compound is 17-48 wt %, based on the weight of the solid form.

It should be noted that, since the molecular-level amide-containing compound is inseparably distributed among the molecular-level biodegradable copolymer, there is a strong dipole-dipole interaction between the biodegradable copolymer and the amide-containing compound.

Figure 2:
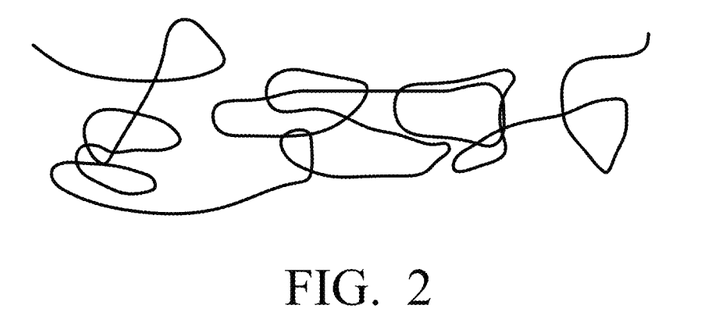
FIG. 2 is a schematic diagram showing the random arrangement structure of the biodegradable copolymer according to an embodiment of the disclosure.
Figure 3:
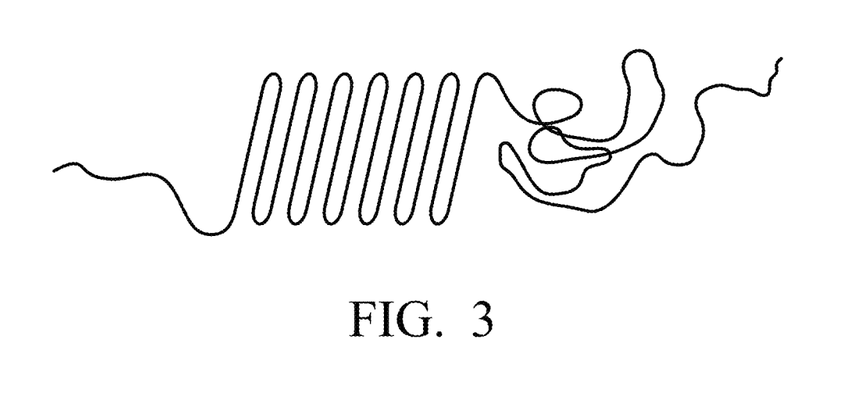
FIG. 3 is a schematic diagram showing the partially regular arrangement structure of the biodegradable copolymer according to an embodiment of the disclosure.

Due to the dipole-dipole interaction, the random arrangement structure (as shown in FIG. 2) of the biodegradable copolymer is altered to a partially regular arrangement structure (as shown in FIG. 3), resulting in the biodegradable copolymer being able to transform from the amorphous state to semi-crystalline state.

Accordingly, the solid form of the disclosure has improved stability, thereby enhancing storage convenience. Further, the solid form of the disclosure can be dissolved completely in water (with a solid content of 40 wt %) within one minute, thereby meeting requirements during clinical surgery.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Preparation of the Solid Form

Example 1

Figure 7:
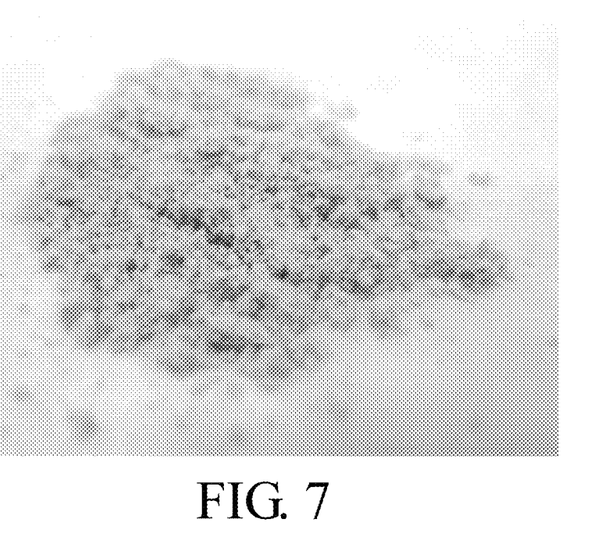
FIG. 7 is a photograph of the solid folio (1) of Example 1.

0.1906 g of an mPEG-PLGA-BOX-PLGA-mPEG polymer (mPEG was methoxy poly(ethylene glycol with a molecular weight of 550 g/mole, and PLGA was ispoly(lactide-co-glycolide) with a molecular weight of 1405 g/mole, and BOX was a residual moiety of 2,2'-Bis(2-oxazoline)), and 0.08 g of urea were dissolved in water and stirred at 4° C., obtaining a solution (with a solid content of 21.3 wt %), wherein the weight ratio of the mPEG-PLGA-BOX-PLGA-mPEG and urea was 70.4:29.6. Next, the aforementioned solution was cooled to −20° C. to form a solid mixture. Finally, the solid mixture was subjected to a freeze-drying process at −20° C. under 8 mTorr for 2 days, obtaining to a solid form (1), as shown in FIG. 7.

Example 2

0.1835 g of an mPEG-PLGA-BOX-PLGA-mPEG polymer (mPEG was methoxy poly(ethylene glycol with a molecular weight of 550 g/mole, PLGA was poly(lactide-co-glycolide) with a molecular weight of 1405 g/mole, and BOX was a residual moiety of 2,2'-Bis(2-oxazoline)) and 0.04 g of urea were dissolved in water and stirred at 4° C., obtaining a solution (with a solid content of 18.27 wt %), wherein the weight ratio of the mPEG-PLGA-BOX-PLGA-mPEG and urea was 82.1:17.9. Next, the aforementioned solution was cooled to −20° C. to form a solid mixture. Finally, the solid mixture was subjected to a freeze-drying process at −20° C. under 8 mTorr for 2 days, obtaining to a solid form (2).

Example 3

0.2188 g of an mPEG-PLGA-BOX-PLGA-mPEG polymer (mPEG was methoxy poly(ethylene glycol with a molecular weight of 550 g/mole, PLGA was poly(lactide-co-glycolide) with a molecular weight of 1405 g/mole, and BOX was a residual moiety of 2,2'-Bis(2-oxazoline)) and 0.24 g of niacinamide were dissolved in water and stirred at 4° C., obtaining a solution (with a solid content of 31.45 wt %), wherein the weight ratio of the mPEG-PLGA-BOX-PLGA-mPEG and niacinamide was 47.7:52.3. Next, the aforementioned solution was cooled to −20° C. to form a solid mixture. Finally, the solid mixture was subjected to a freeze-drying process at −20° C. under 8 mTorr for 2 days, obtaining to a solid form (3).

Example 4

0.1941 g of an mPEG-PLGA-BOX-PLGA-mPEG polymer (mPEG was methoxy poly(ethylene glycol with a molecular weight of 550 g/mole, PLGA was poly(lactide-co-glycolide) with a molecular weight of 1405 g/mole, and BOX was a residual moiety of 2,2'-Bis(2-oxazoline)) and 0.1 g of urea were dissolved in water and stirred at 4° C., obtaining a solution (with a solid content of 22.73 wt %), wherein the weight ratio of the mPEG-PLGA-BOX-PLGA-mPEG and urea was 66:34. Next, the aforementioned solution was cooled to −20° C. to form a solid mixture. Finally, the solid mixture was subjected to a freeze-drying process at −20° C. under 8 mTorr for 2 days, obtaining to a solid form (4).

Example 5

0.1976 g of an mPEG-PLGA-BOX-PLGA-mPEG polymer (mPEG was methoxy poly(ethylene glycol with a molecular weight of 550 g/mole, PLGA was poly(lactide-co-glycolide) with a molecular weight of 1405 g/mole, and BOX was a residual moiety of 2,2'-Bis(2-oxazoline)) and 0.12 g of urea were dissolved in water and stirred at 4° C., obtaining a solution (with a solid content of 24.1 wt %), wherein the weight ratio of the mPEG-PLGA-BOX-PLGA-mPEG and urea was 62.2:37.8. Next, the aforementioned solution was cooled to −20° C. to form a solid mixture. Finally, the solid mixture was subjected to a freeze-drying process at −20° C. under 8 mTorr for 2 days, obtaining to a solid form (5).

Example 6

0.1906 g of an mPEG-PLGA di-block polymer (mPEG was methoxy poly(ethylene glycol with a molecular weight of 550 g/mole, PLGA was poly(lactide-co-glycolide) with a molecular weight of 1405 g/mole) and 0.08 g of urea were dissolved in water and stirred at 4° C., obtaining a solution (with a solid content of 21.3 wt %), wherein the weight ratio of the mPEG-PLGA and urea was 70.4:29.6. Next, the aforementioned solution was cooled to −20° C. to form a solid mixture. Finally, the solid mixture was subjected to a freeze-drying process at −20° C. under 8 mTorr for 2 days, obtaining to a solid form (6).

Example 7

0.1969 g of an mPEG-PLGA di-block polymer (mPEG was methoxy poly(ethylene glycol with a molecular weight of 550 g/mole, PLGA was poly(lactide-co-glycolide) with a molecular weight of 1405 g/mole) and 0.1156 g of urea were dissolved in water and stirred at 4° C., obtaining a solution (with a solid content of 23.81 wt %), wherein the weight ratio of the mPEG-PLGA and urea was 63:37. Next, the aforementioned solution was cooled to −20° C. to form a solid mixture. Finally, the solid mixture was subjected to a freeze-drying process at −20° C. under 8 mTorr for 2 days, obtaining to a solid form (7).

Example 8

0.2047 g of an mPEG-PLGA di-block polymer (mPEG was methoxy poly(ethylene glycol with a molecular weight of 550 g/mole, PLGA was poly(lactide-co-glycolide) with a molecular weight of 1405 g/mole) and 0.16 g of urea were dissolved in water and stirred at 4° C., obtaining a solution (with a solid content of 26.72 wt %), wherein the weight ratio of the mPEG-PLGA and urea was 56.1:43.9. Next, the aforementioned solution was cooled to −20° C. to form a solid mixture. Finally, the solid mixture was subjected to a freeze-drying process at −20° C. under 8 mTorr for 2 days, obtaining to a solid form (8).

Comparative Example 1

Figure 8:
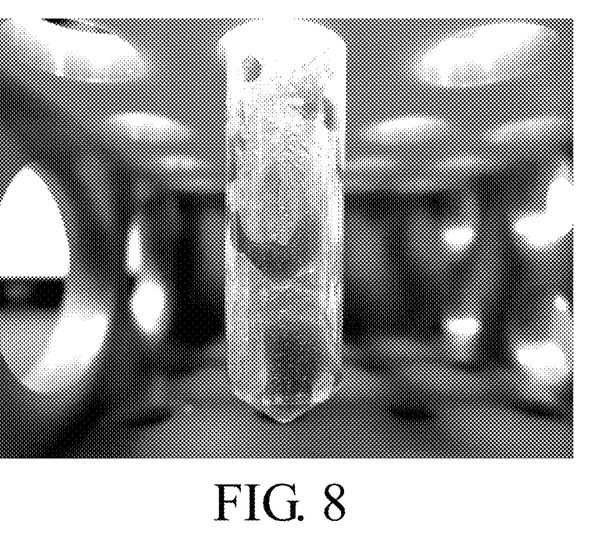
FIG. 8 is a photograph of the mixture (1) of Comparative Example 1.

0.1906 g of an mPEG-PLGA-BOX-PLGA-mPEG polymer (mPEG was methoxy poly(ethylene glycol with a molecular weight of 550 g/mole, PLGA was poly(lactide-co-glycolide) with a molecular weight of 1405 g/mole, and BOX was a residual moiety of 2,2'-Bis(2-oxazoline)) and 0.08 g of urea were mixed and stirred at 25° C., obtaining to a mixture (1), as shown in FIG. 8. The weight ratio of the mPEG-PLGA-BOX-PLGA-mPEG and urea was 70.4:29.6.

Comparative Example 2

The process for comparative Example 2 was performed as Example 1 except for the substitution of the glycine for the urea, obtaining a non-uniform solution. After subjecting the solution to a freeze-drying process, a mixture (2) was obtained.

Comparative Example 3

The process for comparative Example 3 was performed as Example 1 except for the substitution of the L-arginine for the urea, obtaining a non-uniform solution. After subjecting the solution to a freeze-drying process, a mixture (3) was obtained.

Comparative Example 4

The process for comparative Example 3 was performed as Example 1 except for the substitution of the L-Glutamine for the urea, obtaining a non-uniform solution. After subjecting the solution to a freeze-drying process, a mixture (4) was obtained.

Measurement of the Solid Form

Example 9

X-Ray Diffraction Identification

Figure 4:
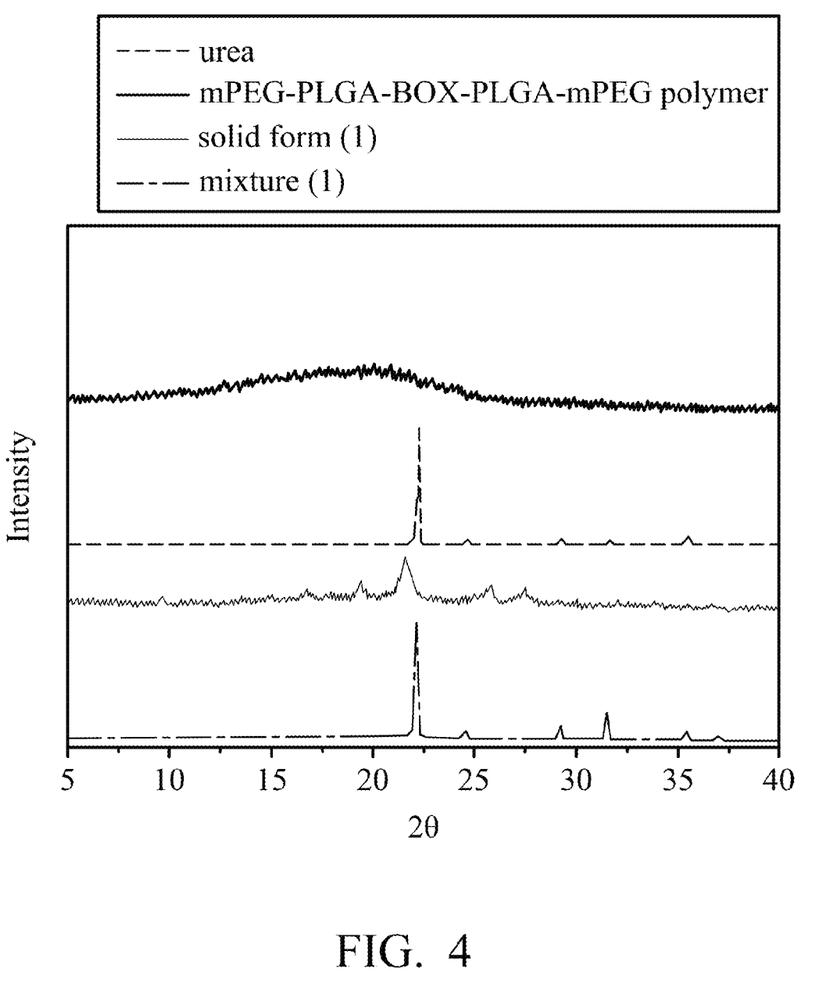
FIG. 4 shows X-ray diffraction profiles of a urea, the mPEG-PLGA-BOX-PLGA-mPEG polymer used in Example 1, the solid form (1) of Example 1, and the mixture (1) of the Comparative Example 1.

A urea, the mPEG-PLGA-BOX-PLGA-mPEG polymer used in Example 1, the solid form (1) of Example 1, and the mixture (1) of the Comparative Example 1 were identified by X-ray diffraction, and the results are shown in FIG. 4.

As shown in FIG. 4, the mPEG-PLGA-BOX-PLGA-mPEG polymer had a broad band at a 2θ angle from 15 to 25, which was a typical amorphous broad hump-peak. The pure urea had peaks at a 2θ angle of 22.3, 24.6, 29.4, 31.6, 35.4, and 37.1, which were crystalline sharp peaks. The solid form (1) of the Example 1 further had new crystalline sharp peaks at a 2θ angle of 19.6, 21.7, 25.8, and 27.5, except for the amorphous broad hump-peak of the mPEG-PLGA-BOX-PLGA-mPEG polymer and the crystalline sharp peaks of the urea.

Due to the freeze-drying process, the urea molecules are inseparably distributed among the mPEG-PLGA-BOX-PLGA-mPEG polymer. There was a strong dipole-dipole interaction between the urea and mPEG-PLGA-BOX-PLGA-mPEG polymer. Therefore, the random arrangement structure of the mPEG-PLGA-BOX-PLGA-mPEG polymer was altered to a partially regular arrangement structure, resulting in the mPEG-PLGA-BOX-PLGA-mPEG polymer transforming from an amorphous state to semi-crystalline state. As a result, due to the semi-crystalline mPEG-PLGA-BOX-PLGA-mPEG polymer, new crystalline sharp peaks (19.6, 21.7, 25.8, and 27.5) appeared in the X-ray diffraction profile of the solid form (1).

To the contrary, since the Comparative Example 1 disclosed directly mixed the mPEG-PLGA-BOX-PLGA-mPEG polymer with the urea at 25° C., the mixture (1) of Comparative Example 1 had the amorphous broad hump-peak of the mPEG-PLGA-BOX-PLGA-mPEG polymer and the crystalline sharp peaks of the urea (there was no peaks observed, at the 2θ angle of 19.6, 21.7, 25.8, and 27.5). Therefore, the mPEG-PLGA-BOX-PLGA-mPEG polymer of the mixture (1) was in an amorphous state, rather than a semi-crystalline state.

Figure 5:
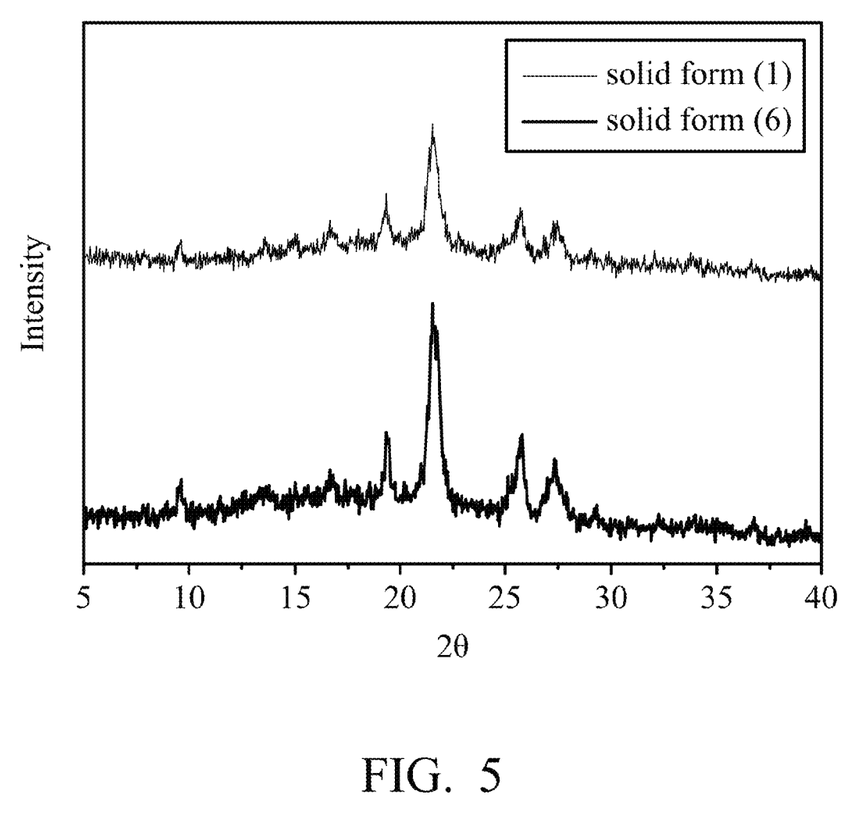
FIG. 5 shows X-ray diffraction profiles of the solid forms (1) and (6) of Examples 1 and 6.

Further, the solid form (6) of Example 6 was identified by X-ray diffraction, and the result is shown in FIG. 5. In comparison with the solid form (1) of Example 1, the solid form (6) also had crystalline sharp peaks at a 2θ angle of 19.6, 21.7, 25.8, and 27.5. Accordingly, the amorphous mPEG-PLGA di-block polymer transited from the amorphous state to the semi-crystalline state.

Figure 6:
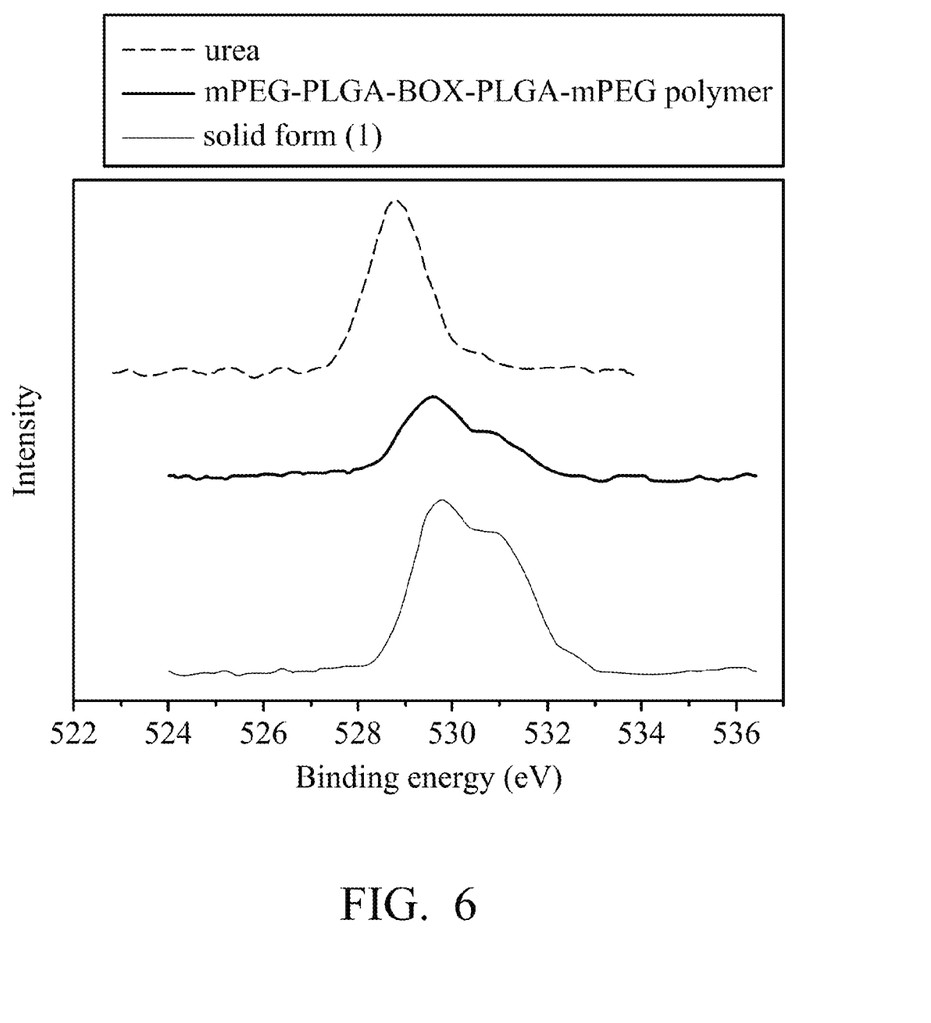
FIG. 6 is an X-ray photoelectron spectrum showing the binding energies (O1S) of a urea, the mPEG-PLGA-BOX-PLGA-mPEG polymer used in Example 1, and the solid form (1) of Example 1.

Moreover, the binding energies (O1s) of the urea, the mPEG-PLGA-BOX-PLGA-mPEG polymer used in Example 1, and the solid form (1) of Example 1 were measured by an X-ray photoelectron spectroscopy, and the results are shown in FIG. 6.

As shown in FIG. 6, the urea had a binding energy (O1s) main peak at 528.8 eV, and the mPEG-PLGA-BOX-PLGA-mPEG polymer had binding energy (O1s) main peaks at 529.6 eV and 530.6 eV. Further, the solid form (1) of Example 1 had binding energy (O1s) main peaks at 529.8 eV and 530.8 eV. Accordingly, there was a strong dipole-dipole interaction between the urea and mPEG-PLGA-BOX-PLGA-mPEG polymer in the solid form (1), forcing the binding energy (O1s) main peaks of the mPEG-PLGA-BOX-PLGA-mPEG polymer to migrate from 529.6 eV and 530.6 eV to 529.8 eV and 530.8 eV.

Example 10

Thermal Sensitivity Test 0.15 g of the solid form (1) of Example 1 was dissolved in Dulbecco's Phosphate-Buffered Saline (0.85 ml, (no calcium, no magnesium, 1×), obtaining a hydrogel. After measuring, the obtained hydrogel exhibited thermal sensitivity at 37.

Example 11

Dissolution Rate Test

The mPEG-PLGA-BOX-PLGA-mPEG polymer used in Example 1, the mPEG-PLGA di-block polymer used in Example 4, the solid forms (1)-(8) of Example 1-8, and the mixtures (1)-(4) of Comparative Example 1-4 were added in water respectively, to obtain aqueous solutions (with a solid content of 40 wt %). The aqueous solutions were stirred at 25° C., and the dissolving time was measured. The results are shown in Table 1.

TABLE 1

|  | dissolving time | hydrogel |
| --- | --- | --- |
| mPEG-PLGA-BOX-PLGA-mPEG polymer | 6 days | Yes |
| mPEG-PLGA di-block polymer | 1 day | Yes |
| solid form (1) | less than 10 sec | Yes |
| solid form (2) | less than 10 sec | Yes |
| solid form (3) | less than 1 min | No |
| solid form (4) | less than 10 sec | Yes |
| solid form (5) | less than 10 sec | Yes |
| solid form (6) | less than 10 sec | Yes |
| solid form (7) | less than 10 sec | Yes |

TABLE 1-continued

|  | dissolving time | hydrogel |
| --- | --- | --- |
| solid form (8) | less than 10 sec | Yes |
| mixture (1) | 24 hrs | Yes |
| mixture (2) | 11 days | No (forming a hydrogel under 4° C.) |
| mixture (3) | 3 days | No (forming a hydrogel under 4° C.) |
| mixture (4) | 1 day | No |

As shown in Table 1, the solid forms (1)-(8) of the disclosure Example 1-8 were dissolved completely in water within 5 min, resulting in convenience to users. To the contrary, in comparison with Example 1, the mixture (1) of Comparative Example 1 having the same starting materials (mPEG-PLGA-BOX-PLGA-mPEG polymer and urea) dissolved completely in water after stirring for about 24 hrs. Further, Comparative Examples 2-4 employed various compounds for substitution of the urea or niacinamide, but the mixtures of Comparative Examples 2-4 did not dissolve completely in water within 5 min.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A freeze-dried solid form consisting essentially of a biodegradable copolymer and an amide compound, wherein the biodegradable copolymer has a structure represented by Formula (I) or Formula (II):

A-B-BOX-B-A      Formula (I); and

B-A-B-(BOX-B-A-B)$_n$-BOX-B-A-B      Formula (II)

wherein A comprises a hydrophilic block of polyethylene glycol polymer, B comprises a hydrophobic block of polyester polymer, BOX is a bifunctional group monomer of 2,2'-Bis(2-oxazoline) and used for coupling the blocks A-B or B-A-B, and n is an integer and the same or more than 0;

wherein the amide compound is selected from the group consisting of:

and combinations thereof; and wherein the biodegradable copolymer is semi-crystalline due to the dipole-dipole interaction between the biodegradable copolymer and the amide compound.

2. The solid form as claimed in claim 1, wherein the hydrophilic block of polyethylene glycol polymer comprises polyethylene glycol (PEG) or methoxy-poly(ethylene glycol) (mPEG).

3. The solid form as claimed in claim 1, wherein the hydrophobic block of polyester polymer comprises poly(lactide-co-glycolide) (PLGA), poly(propionic-co-lactic (PPLA), poly(valeric-co-lactic) (PVLA), or poly(caproic-co-lactic) (PCLA).

4. The solid form as claimed in claim 1, wherein the weight ratio of the biodegradable copolymer is 52-83 wt %, and the weight ratio of the amide compound is 17-48 wt %, based on the weight of the solid form.

5. The solid form as claimed in claim 1, wherein the solid form is completely dissolved in water within 5 min.

6. The solid form as claimed in claim 1, wherein the solid is prepared by a method comprising:
dissolving the biodegradable copolymer and the amide compound in water at a first temperature, obtaining a solution;
cooling the solution at a second temperature to form a solid mixture; and
freeze-drying the solid mixture at a third temperature.

* * * * *